(12) United States Patent
Thadhani et al.

(10) Patent No.: US 7,323,346 B2
(45) Date of Patent: Jan. 29, 2008

(54) SCREENING FOR GESTATIONAL DISORDERS

(75) Inventors: Ravi I. Thadhani, Boston, MA (US); Myles S. Wolf, Brookline, MA (US); Tanya Lynn Knickerbocker, Brighton, MA (US); Gavin MacBeath, Arlington, MA (US)

(73) Assignees: The General Hospital Corporation, Boston, MA (US); Harvard University, Cambridge, MA (US)

( * ) Notice: Subject to any disclaimer, the term of this patent is extended or adjusted under 35 U.S.C. 154(b) by 40 days.

(21) Appl. No.: 10/920,116

(22) Filed: Aug. 16, 2004

(65) Prior Publication Data

US 2005/0148023 A1 Jul. 7, 2005

Related U.S. Application Data

(60) Provisional application No. 60/495,501, filed on Aug. 14, 2003.

(51) Int. Cl.
*G01N 33/543* (2006.01)
*G01N 33/53* (2006.01)

(52) U.S. Cl. .......... 436/518; 435/7.1; 436/811
(58) Field of Classification Search ........ 436/518, 436/524, 16, 811, 86; 435/7.1, 7.92, 811; 422/61; 530/388.23, 389.2
See application file for complete search history.

(56) References Cited

U.S. PATENT DOCUMENTS

| | | | |
|---|---|---|---|
| 5,516,702 A * | 5/1996 | Senyei et al. ........... | 436/510 |
| 5,580,554 A | 12/1996 | Keith | |
| 6,461,830 B1 | 10/2002 | Parrott | |
| 2002/0102530 A1 | 8/2002 | Keith, Jr. et al. | |
| 2002/0110833 A1 | 8/2002 | Caniggia et al. | |
| 2004/0053325 A1* | 3/2004 | Breit et al. ............. | 435/7.1 |
| 2004/0126828 A1* | 7/2004 | Karumanchi et al. .... | 435/7.92 |

OTHER PUBLICATIONS

Janeway C, Travers P, Walport M, Capra JD. 1999. Immunobiology: The Immune System in Health and Disease. New York, NY: Elsevier Science Ltd./Garland Publishing, pp. 197-198, 266-269, 288-293, 588-591, 593, 598, and 604.*
Bowen et al. "Cytokines of the Placenta and Extra-placental Membranes: Roles and Regulation During Human Pregnancy and Parturition" (2002) Placenta 23:257-273.*
Stiemer et al. "Interleukin-8 in urine: a new diagnostic parameter for intra-amniotic infection after premature rupture of the membranes" (1997) British Journal of Obstetrics and Gynaecology 104:499-502.*
Kauma et al. "Increased Endothelial Monocyte Chemoattractant Protein-1 and Interleukin-8 in Preeclampsia" (2002) Obstet Gynecol. 100:706-714.*

The American Physiological Society, "Guidelines for Reporting Statistics in Journals Published by the American Physiological Society" J Neurophysiol 92:669-671, 2004.*
Tikhonov et al., "A study of interleukin-8 and defensins in urine and plasma of patients with pyelonephritis and glomerulonephritis" Neph. Dial. Transplant. 12(12):2557-61 (1997).
Djurovic et al., "Absence of enhanced systemic inflammatory response at 18 weeks of gestation in women with subsequent pre-eclampsia," BJOG 109(7):759-64 (2002).
Bartha et al., "The relationships between leptin and inflammatory cytokines in women with pre-eclampsia," *British Journal of Obstetrics and Gynaecology*, 108:1272-1276 (2001).
Benyo et al., "Expression of Inflammatory Cytokines in Placentas from Women with Preeclampsia," *J. Clin. Endocrinol. Metab.*, 86(6):2505-2512 (2001).
Benyo et al., "Hypoxia Stimulates Cytokine Production by Villous Explants from the Human Placenta," *J. Clin. Endocrinol. Metab.*, 82(5):1582-1588 (1997).
Denison et al., "Cytokine secretion by human fetal membranes, deciduas and placenta at term," *Hum. Reprod.*, 13(12):3560-3565 (1998).
"Findings from the 1992-98 Patient Outcomes Research Team on Low Birthweight," Agency for Healthcare Research and Quality, http://www.ahcpr.gov/clinic/lobrhigh.htm, 3 pages (May 28, 2003).
Hæger et al., "Increased release of tumor necrosis factor-alpha and interleukin-6 in women with the syndrome of hemolysis, elevated liver enzymes, and low platelet count," *Acta. Obstet. Gynecol. Scand.*, 75:695-701 (1996).
Lappas et al., "Regulation of Proinflammatory Cytokines in Human Gestational Tissues by Peroxisome Proliferator-Activated Receptor-γ. Effect of 15-Deoxy-$\Delta^{12,14}$-$PGJ_2$ and Troglitazone," *J. Clin. Endocrinol. Metab.*, 87(10):4667-4672 (2002).
Matthiesen, "Immune Changes in Pregnancy—A Survey of some Immunological Variables in Normal and Complicated Pregnancies," Linköping University Medical Dissertations No. 563, http://www.bibl.liu.se/liupubl/disp/disp98/med563s.htm, 2 pages (May 28, 2003).
Omu et al., "Connection between human leucocyte antigens D region and T helper cytokines in preeclampsia," *Arch. Gynecol. Obstet.*, 269(2):79-84 (2004; published online Nov. 7, 2002).
Smulian et al., "Intrapartum fever at term: Serum and histologic markers of inflammation," *Am. J. Obstet. Gynecol.*, 188(1):269-274 (2003).
Takacs et al., "Increased vascular endothelial cell production of interleukin-6 in severe preeclampsia," *Am. J. Obstet. Gynecol.*, 188(3):740-744 (2003).
Velzing-Aarts et al., "High Serum Interleukin-8 Levels in Afro-Caribbean Women with Pre-eclampsia. Relations with Tumor Necrosis Factor-α, Duffy Negative Phenotype and Von Willebrand Factor," *Am. J. Reprod. Immunol.*, 48:319-322 (2002).

(Continued)

*Primary Examiner*—Long V. Le
*Assistant Examiner*—Christine Foster
(74) *Attorney, Agent, or Firm*—Fish & Richardson P.C.

(57) ABSTRACT

The invention relates to methods and compositions for identifying pregnant subjects having, or predisposed to having, gestational diabetes, preeclampsia, and gestational hypertension. The methods are applicable to urine and/or blood samples and can be conducted prior to the third trimester of pregnancy, and as early as the first trimester.

26 Claims, 5 Drawing Sheets
(1 of 5 Drawing Sheet(s) Filed in Color)

OTHER PUBLICATIONS

Seely and Solomon, "Insulin Resistance and its Potential Role in Pregnancy-Induced Hypertension," *The Journal of Clinical Endocrinology & Metabolism*, vol. 88(6), pp. 2393-2398, (2003).

Levine et al., "Circulating Angiogenic Factors and the Risk of Preeclampsia," *The New England Journal of Medicine*, vol. 350, pp. 672-683, (2004).

Polliotti et al., "Second-Trimester Maternal Serum Placental Growth Factor and Vascular Endothelial Growth Factor for Predicting Severe, Early-Onset Preeclampsia," *The American College of Obstetricians and Gynecologists*, vol. 101, No. 6, pp. 1266-1274, (2003).

Taylor et al., "Longitudinal Serum Concentrations of Placental Growth Factor: Evidence for Abnormal Placental Angiogenesis in Pathologic Pregnancies," *American Journal Obstetricians and Gynecologists*, vol. 188, pp. 177-182 (2003).

Thadhani et al., "Insulin Resistance and Alternations in Angiogenesis Additive Insults That May Lead to Preeclampsia," *Hypertension*, vol. 43, pp. 988-992, (2004).

Tidwell et al., "Low Maternal Serum Levels of Placenta Growth Factor as an Antecedent of Clinical Preeclampsia," *American Journal Obstetricians and Gynecologists*, vol. 184, pp. 1267-1272 (2001).

Wolf et al., "First Trimester Insulin Resistance and Subsequent Preeclampsia: A Prospective Study," *The Journal of Clinical Endocrinology & Metabolism*, vol. 87(4), pp. 1563-1568, (2002).

Wolf et al., "Insulin Resistance But Not Inflammation is Associated with Gestational Hypertension," *Hypertension*, vol. 40, pp. 886-891, (2002).

Wolf et al., "Preeclampsia and Future Cardiovascular Disease: Potential Role of Altered Angiogenesis and Insulin Resistance," *The Journal of Clinical Endocrinology & Metabolism*, vol. 89(12), pp. 6239-6243, (2004).

Rinehart et al., "Expression of the Placental Cytokines Tumor Necrosis Factor α, Interleukin 1β, and Interleukin 10 is Increased in Preeclampsia," *Am J Obstet Gynecol*, Oct. 1999, pp. 915-920.

Thadhani et al., "First Trimester Placental Growth Factor and Soluble Fms-Like Tyrosine Kinase 1 and Risk for Preeclampsia," *The journal of Clinical Endocrinology & Metabolism*, 89(2), pp. 770-775, 2004.

Maynard et al., "Excess Placental Solube Fms-Like Tyrosine Kinase 1 (sFlt1) may Contribute to Endothelial Dysfunction, Hypertension, and Proteinuria in Preeclampsia," *The Journal of Clinical Investigation*, Mar. 2003, vol. 111, No. 5, pp. 1-10.

Page et al., "Placental Peptides as Markers of Gestational Disease," *Reproduction* (2002) 123, 487-495.

Massé et al., "A Prospective Study of Several Potential Biologic Markers for Early Prediction of the Development of Preeclampsia," *Am J Obstet Gynecol*, vol. 169, No. 3, pp. 501-508, 1993.

Heikkinen et al., "Cytokine Levels in Midtrimester Amniotic Fluid in Normal Pregnancy and in the Prediction of Pre-Eclampsia," *Scand. J. Immunol*, 53, 310-314, 2001.

Helske et al., "Expression of Vascular Endothelial Growth Factor Receptors 1, 2 and 3 in Placentas From Normal and Complicated Pregnancies," *Molecular Human Reproduction*, vol. 7, No. 2, pp. 205-210, 2001.

* cited by examiner

Figure 2

| +/- I | IL-6 | IL-6 + I | IL-8 | IL-8 + I | MCP | MCP + I |
|---|---|---|---|---|---|---|
| Patient 1 | 1.3 | 1.0 | 2.6 | 2.6 | 1.6 | 1.5 |
| Patient 2 | 1.0 | 1.1 | 2.1 | 2.0 | 1.9 | 1.9 |
| Patient 3 | 0.8 | 0.8 | 2.5 | 2.7 | 1.5 | 1.4 |
| Patient 4 | 3.3 | 3.5 | 2.2 | 2.0 | 4.3 | 4.3 |
| Patient 5 | 1.1 | 0.9 | 2.5 | 2.7 | 1.5 | 1.3 |

Figure 3

| Reproducibility | IL-6 (1) | IL-6 (2) | IL-8 (1) | IL-8 (2) | MCP (1) | MCP (2) |
|---|---|---|---|---|---|---|
| Patient 1 | 1.3 | 1.3 | 2.6 | 2.4 | 1.6 | 1.8 |
| Patient 2 | 1.0 | 1.3 | 2.2 | 2.2 | 1.8 | 1.9 |
| Patient 3 | 0.8 | 0.9 | 2.5 | 2.4 | 1.6 | 1.4 |
| Patient 4 | 3.5 | 3.4 | 2.2 | 2.1 | 4.6 | 4.3 |
| Patient 5 | 1.1 | 1.2 | 2.7 | 2.5 | 1.4 | 1.5 |

Figure 4

| SERUM | PlGF* pg/ml | sFlt-1 pg/ml | Ratio (sFlt-1/PlGF) |
|---|---|---|---|
| Controls | 163 | 478 | 3 |
| GDM | 34 | 723 | 21 |
| PE | 26 | 1176 | 45 |

Figure 5

| URINE | PlGF* pg/g Cr | IL-6* pg/g Cr | MCP-1* pg/g Cr |
|---|---|---|---|
| PE | 53.7 | 40.7 | 494 |
| Controls | 71.9 | 10.9 | 244 |

*Normalized for urine creatinine

| Postpartum Pilot | GDM | PE | UP |
|---|---|---|---|
| Age (yrs) | 27 | 33 | 32 |
| BMI (kg/m$^2$) | 27 | 26 | 25 |
| CRP (mg/L) | 1.2 | 1.4 | 0.6 |
| IL-6 (pg/ml) | 2.1 | 1.9 | 1.1 |
| Fasting Glucose (mmol) | 5 | 4.7 | 4.4 |
| Fasting Insulin (pmol/L) | 84 | 84 | 66 |
| HOMA$_{IR}$ | 3.12 | 2.86 | 1.96 |
| $\Delta I_{30}/\Delta G_{30}$ (pmol/mmol) | 104 | 180 | 147 |

HOMA-IR = (fasting insulin x fasting glucose)/22.5)
$\Delta I_{30}/\Delta G_{30}$ (pmol/mmol)first-phase insulin secretion

| Cases:Controls 1:1 | Power | | |
|---|---|---|---|
| SD | 0.75 | 1.0 | 1.25 |
| N=50 | 0.82 | 0.98 | 1.0 |
| N=60 | 0.90 | 1.0 | 1.0 |
| N=70 | 0.95 | 1.0 | 1.0 |

| Cases:Controls 1:3 | Power | | |
|---|---|---|---|
| RR | 2.5 | 3.0 | 3.5 |
| N=60 | 0.81 | 0.87 | 0.94 |

SCREENING FOR GESTATIONAL DISORDERS

CROSS-REFERENCE TO RELATED APPLICATION

This application claims priority from U.S. Provisional Patent Application No. 60/495,501, filed on Aug. 14, 2003, the contents of which is incorporated herein by reference in its entirety.

STATEMENT AS TO FEDERALLY SPONSORED RESEARCH

This invention was made with Government support under HD39223 awarded by the National Institutes of Health. Thus, the Government has certain rights in the invention.

TECHNICAL FIELD

This invention relates to screening for gestational disorders, and more particularly to screening for biomarkers present in a biological sample obtained from a pregnant subject that are indicative of a gestational disorder.

BACKGROUND

Gestational diabetes mellitus (GDM) and pregnancy-induced hypertension (PIH) complicate 2-3% and 5-10% of all pregnancies, respectively. These disorders can occur in the third-trimester of pregnancy and are associated with significant maternal and fetal morbidity and mortality. Gestational diabetes has been described as the new onset or new diagnosis of glucose intolerance during pregnancy and is associated with fetal complications relating to macrosomia, such as shoulder dystocia and birth trauma. In addition, GDM is associated with increased cesarean section rates and increased risk of PIH. PIH is associated with preterm labor, increased cesarean section rates, acute renal failure, hepatic dysfunction, stroke, coagulopathy, and death. For the fetus, PIH is associated with low birth weight, extended neonatal intensive care, and intrauterine death.

Prospective studies suggest chronic subclinical inflammation, whether measured in a global fashion with c-reactive protein (CRP) or with specific cytokines, is an important risk factor for type 2 diabetes mellitus. Elevated high sensitivity-CRP levels in the first trimester may be indicative of increased risk for developing GDM. Thus, inflammatory markers and measures of insulin resistance measured in blood early in gestation may be associated with subsequent development of GDM and/or PIH. While serum CRP results have been positive, measurement of inflammatory markers limits the potential understanding of the inflammatory repertoire associated with these outcomes in pregnancy. Furthermore, CRP remains a biomarker, and not a cytokine potentially involved in the pathogenesis of disease. Finally many studies are done at the time of preeclampsia and not before, so their predictive power is limited.

Individuals at increased risk of developing preeclampsia and eclampsia include primigravidas and women with multiple gestations, molar pregnancy or fetal hydrops, chronic hypertension or diabetes, or a personal or family history of eclampsia or preeclampsia. Preeclampsia (PE) and gestational hypertension (GH) are forms of PIH. Preeclampsia is generally defined as the combination of high blood pressure (hypertension), swelling (edema), and protein in the urine (albuminuria, proteinuria) developing after the 20th week of pregnancy. Preeclampsia ranges in severity from mild to severe; the mild form is sometimes called proteinuric pregnancy-induced hypertension or proteinuric gestational hypertension. Gestational (transient) hypertension is generally characterized as the acute onset of hypertension in pregnancy or the early puerperium without proteinuria or abnormal edema and resolving within 10 days after delivery. Chronic hypertension that had been latent prior to the pregnancy may also become evident during gestation. Pregnant women with latent chronic hypertension are also at increased risk for stillbirth, neonatal death, and other fetal complications, but the risk is much lower than that of women with preeclampsia or eclampsia. Women with transient or latent chronic hypertension are also more likely to develop chronic hypertension in later years.

In general, the definition of GDM provides that two or more of the following blood glucose values meet or exceed the following thresholds: fasting, 95 mg/dl (5.3 mmol/L); 1 hour 180 mg/dl (10.0 mmol/L); 2 hours, 155 mg/dl (8.6 mmol/L); 3 hours, 140 mg/dl (7.8 mol/L). Alternatively, testing can be performed in a single step using only the 75-100 gm oral glucose tolerance test (OGTT) without prior glucose screening. In either case, the definition of GDM can be based on the results of the 75-100 gm OGTT.

The present standard therapy for PIH, including PIH resulting from GDM, is delivery, often at the expense of fetal well-being. Prophylactic strategies to prevent PIH, including calcium supplementation and aspirin therapy, have been mostly unsuccessful. One reason these trials have failed is that the absence of screening tests limited the ability to administer the therapeutic interventions early enough to modify pregnancy outcome. For example, diagnosing PE by the appearance of edema and proteinuria alone is unreliable as edema is common in normal pregnancies and measurable proteinuria usually occurs only after hypertension is manifested. Therefore, such a test lacks specificity and fails to detect GDM or PIH prior to manifestation of the disease in the third trimester of pregnancy.

Currently, no single biochemical marker, or plurality of biochemical markers, reliably identifies women at risk for developing GDM or PIH prior to the third trimester of pregnancy. Thus, there exists a need for diagnostic methods and compositions that lead to early implementation of therapy and improved pregnancy outcomes for women at risk for gestational disorders.

SUMMARY

The invention is based, in part, on the discovery that certain cytokines and/or growth factors can be used as early indicators for the risk of developing a gestational disorder such as gestational diabetes mellitus (GDM) and/or pregnancy induced hypertension (PIH).

The invention provides methods of determining whether a pregnant subject has, or is predisposed to having, a gestational disorder. The methods include generating a subject profile by obtaining a urine sample from the pregnant subject, measuring the level of at least one cytokine in the sample, and comparing the cytokine level in the urine sample with a predetermined reference profile. A reference profile can include a profile generated from one or more pregnant women having a gestational disorder or a profile generated from one or more pregnant women having a normal pregnancy.

In one aspect, the gestational disorder is pregnancy-induced hypertension, such as preeclampsia or gestational hypertension. In another aspect, the gestational disorder is gestational diabetes mellitus. In general, the sample is obtained prior to the third trimester of pregnancy. The cytokine can be an immune/hematopoietin, an interferon, a tumor necrosis factor (TNF)-related molecule or a chemokine. Examples include, e.g., interleukin (IL)-6, IL-8, IL-1β, monocyte chemoattractant protein-1 (MCP-1), or TNF-α, or any combination thereof. A reference profile can be generated from a sample obtained from any source containing, or believed to contain, a cytokine. For example, the reference profile can be obtained from the urine, serum, plasma, amniotic fluid or placental tissue of a reference subject. A reference subject can be a pregnant individual having a gestational disorder and pregnant individual having a normal pregnancy. In another aspect, the method further includes measuring the level of at least one growth factor derived from urine, blood, serum amniotic fluid or placental tissue.

Also provided are methods for identifying a gestational disorder by obtaining a biological sample from a pregnant subject; measuring the level of IL-1α, IL-1β, IL-2, IL-4, IL-11, IL-12, IFN-γ, TNF-α, TNF-R, IL-6, IL-8, VCAM, MCP-1, or Ang-1, or any combination thereof (e.g., IL-6, IL-8, and MCP-1; IL-8, and IL-1α or IL-1β in the sample; and comparing the cytokine level in the sample from the pregnant subject with the cytokine level in a biological sample obtained from 1) a reference subject having a gestational disorder; 2) a reference subject having a normal pregnancy; or 3) both the reference subject having a gestational disorder and the reference subject having a normal pregnancy.

The invention further includes methods for detecting a gestational disorder in a pregnant subject by obtaining a subject profile that includes the level of at least two cytokines detected in a urine sample from a subject and comparing the subject profile to a reference profile that includes the level of at least two cytokines detected in a urine sample obtained from a normal pregnant subject.

The methods of the invention can be accomplished by contacting a urine sample obtained from a pregnant subject with an array of immobilized cytokine-specific biomolecules and detecting a modification of the cytokine-specific biomolecules. The modification is indicative of the level of a cytokine in a sample and can include stable or transient binding of the biomolecule to a cytokine. The subject urine cytokine levels can be compared to reference cytokine levels obtained from reference subjects. Reference cytokine levels can further be used to generate a reference profile from one or more reference subjects. Alternatively, the subject urine cytokine levels can be compared to the cytokine levels in a non-urine sample obtained from a pregnant subject. In one aspect, the cytokine-specific biomolecules are antibodies, such as monoclonal antibodies. In another aspect, the cytokine-specific biomolecules are antigens, such as viral antigens that specifically recognize cytokines. In yet another aspect, the cytokine-specific biomolecules are receptors.

An array of the invention generally includes a substrate having a plurality of addresses, each address having disposed thereon a set of one or more biomolecules, and each biomolecule in the set at a given address specifically detecting the same cytokine; wherein the array includes sufficient addresses to detect at least Ang, sICAM-1, IFN-γ, IL-1α, IL-1β, IL-2, IL-4, IL-6, IL-8, IL-11, IL-12(p70), MCP-1, MCSF, MIP-1a, MIP-1β, PlGF, RANTES, TGF-β1, TGF-β3, sTNFRI, sTNFRII, VCAM-1, VEGF, and sFlt-1. In one aspect, the new arrays can further include an address having disposed thereon an immobilized growth factor-specific biomolecule (or set of biomolecules) that specifically detects at least one growth factor, such as, for example, soluble fms-like tyrosine kinase-1 receptor (sFlt-1), vascular endothelial growth factor (VEGF), placental growth factor (PlGF), or fibroblast growth factor (FGF)-2.

The invention also features a pre-packaged diagnostic kit for detecting a gestational disorder. The kit can include an array as described above and instructions for using the array to test a urine sample to detect a gestational disorder. The array can also be used to determine the efficacy of a therapy administered to treat a gestational disorder by contacting the array with a urine sample obtained from a pregnant patient undergoing therapy for a gestational disorder. The level of at least one cytokine in the sample can be determined and compared to the level of at least one cytokine detected in a urine sample obtained from the patient prior to, or subsequent to, the administration of the therapy. Subsequently, a caregiver can be provided with the comparison information for further assessment.

Further, a subject profile can be entered into a computer system that contains, or has access to, a database that includes a plurality of digitally encoded reference profiles (e.g., a computer-readable medium including such databases). Each profile of the plurality has a plurality of values, each value representing a level of a specific cytokine detected in urine of a pregnant individual having, or pre-disposed to having, a gestational disorder. In this manner, a single subject profile can be used to identify a subject at risk for developing a gestational disorder based upon reference values.

Thus, the invention also features a computer system for determining whether a pregnant subject has, or is predisposed to having, a gestational disorder. The system includes a database that has a plurality of digitally-encoded reference profiles, wherein each profile of the plurality has a plurality of values, each value representing a level of a specific cytokine detected in urine of one or more pregnant individuals having a gestational disorder (or known not to have a gestational disorder); and a server including a computer-executable code for causing the computer to: i) receive a profile of a pregnant subject including the level of at least one cytokine detected in a urine sample from the subject; ii) identify from the database a matching reference profile that is diagnostically relevant to the pregnant subject profile; and iii) generate an indication of whether of the subject has, or is predisposed to having, a gestational disorder.

In general, the invention features methods and compositions for determining a woman's risk of developing preeclampsia, gestational diabetes, and/or gestational hypertension during pregnancy, by obtaining a biological sample, such as urine or blood, from a pregnant woman prior to the third trimester of pregnancy (e.g., at 5 weeks after conception, or at any time between 6 to 24 weeks after conception e.g., 8, 10, 12, 14, 16, 18, or 20 weeks); and measuring the level of a cytokine and/or growth factor in the sample; wherein the level of a cytokine or growth factor in the sample indicates the level of risk of developing preeclampsia, gestational diabetes, and/or gestational hypertension. In this method, the sample can be a non-fasting sample.

In addition to their use to identify women who are at risk, the new methods can be used as a routine screen or "prescreen" for all pregnant women to identify those women who are not at risk for gestational complications, thus avoiding the need for additional testing later during pregnancy. The methods can also be used to determine whether a given therapy is effective, by comparing pre-therapy levels of one or more cytokines with therapy or post-therapy levels.

As used herein, the terms "biological molecules" and "biomolecules" may be used interchangeably. These terms are meant to be interpreted broadly, and generally encompass polypeptides, peptides, oligosaccharides, polysaccharides, oligopeptides, proteins, oligonucleotides, and polynucleotides. Oligonucleotides and polynucleotides include, for example, DNA and RNA, e.g., in the form of aptamers. Biomolecules also include organic compounds, organometallic compounds, salts of organic and organometallic compounds, saccharides, amino acids, nucleotides, lipids, carbohydrates, drugs, steroids, lectins, vitamins, minerals, metabolites, cofactors, and coenzymes. Biomolecules further include derivatives of the molecules described. For example, derivatives of biomolecules include lipid and glycosylation derivatives of oligopeptides, polypeptides, peptides, and proteins, such as antibodies. Further examples of derivatives of biomolecules include lipid derivatives of oligosaccharides and polysaccharides, e.g., lipopolysaccharides.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

The patent or application file contains at least one drawing executed in color. Copies of this patent or patent application publication with color drawing(s) will be provided by the Office upon request and payment of the necessary fee.

FIG. 2 is a table providing data regarding the recovery of cytokines from urine samples in the presence or absence of a protease inhibitor.

FIG. 3 is a table providing data regarding the reproducibility of identifying cytokines in a biological sample using a cytokine array.

FIG. 4 is a table providing data regarding the ratio of sFlt-1/PlGF in the serum of pregnant subjects.

FIG. 5 is a table providing data regarding the correlation of cytokine levels and growth factor levels in the identification of a gestational disorder.

DETAILED DESCRIPTION

Figure 1:
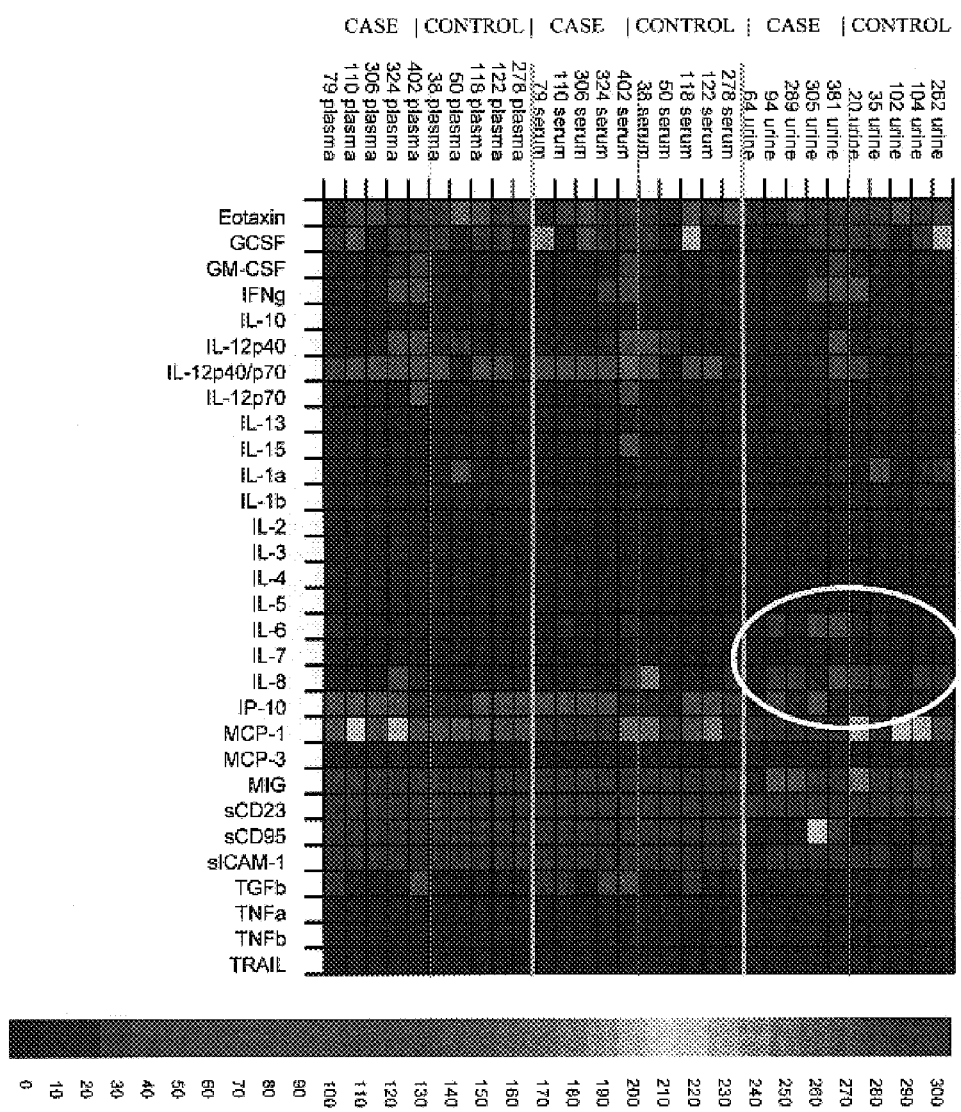
FIG. 1 is a heat map of a cytokine array that depicts the correlation between cytokine levels in urine and the risk of developing a gestational disorder.

Gestational disorders such as pregnancy-induced hypertension (PIH) and gestational diabetes mellitus (GDM) occur in the third-trimester of pregnancy and are associated with significant maternal and fetal morbidity and mortality. Currently there are no effective laboratory tests to predict the incidence of either disorder early in pregnancy. Diagnoses are generally made during the third trimester when symptoms arise or during routine blood pressure and blood glucose screening. The critical absence of diagnostic tests to predict these disorders has hindered the ability of investigators to identify preventive therapeutic agents; current preventive strategies have failed in large part because these interventions were initiated late in pregnancy when the possibility to alter pregnancy outcomes is limited. Furthermore, the absence of early predictive markers limits clinicians' ability to implement preventive therapies in high-risk women.

As discussed in further detail below, the invention is based, in part, on the discovery that a change in cytokine and/or growth factor levels, or antagonist thereof, in urine and/or blood prior to the third trimester of pregnancy, and as early as the first trimester, can be indicative of increased risk of preeclampsia, gestational hypertension and gestational diabetes. Methods of determining whether a pregnant subject has, or is predisposed to having, a gestational disorder are provided. In addition, compositions for determining a subject's risk for developing are provided.

Methods of Identifying At-Risk Subjects

Specific alterations in inflammatory and insulin resistance cytokines (IL-1α, IL-1β, IL-2, IL-4, TNF-α, TNF-R, IL-6, MCP-1, IL-8, IL-11, IL-12, and VCAM), and angiogenesis related growth factors (PlGF, FGF-2) and a growth factor antagonist (sFlt-1) are biologically linked to gestational disorders such as GDM and PIH. In any event, these cytokines, chemokines, and angiogenesis related growth factors, or antagonists thereof, serve as early biomarkers for disease, and after pregnancy, characterize women at high risk for future disease. In one embodiment, a method for determining a predisposition to a gestational disorder includes generating a subject profile by obtaining a urine sample from the pregnant subject, measuring the level of at least one cytokine in the sample, and comparing the cytokine level in the urine sample with a predetermined reference profile. A "gestational disorder" as used herein includes pregnancy-induced hypertension (PIH), such as preeclampsia (PE) or gestational hypertension (GH). A gestational disorder further includes gestational diabetes mellitus (GDM). A "normal" pregnancy, as used herein, is a pregnancy that is not associated with a gestational disorder.

A "subject" profile can also be referred to as a "test" profile. A subject profile can be generated from a sample taken from a subject prior to the third trimester to identify the subject's risk of developing GDN and/or PIH. Thus, a "subject" profile is generated from a subject being tested for a gestational disorder.

A "reference" can also be referred to as a "control" profile. A reference profile can be generated from a sample taken at a particular time point in the pregnancy of a normal individual or from an individual having a gestational disorder. The reference profile, or plurality of reference profiles, can be used to establish threshold values for the levels of, for example, specific cytokines in a sample. A "reference" profile includes a profile generated from one or more pregnant women having a gestational disorder or a profile generated from one or more pregnant women having a normal pregnancy.

A reference profile can be in the form of an array "signature" or "pattern" of specific identifiable biomarkers. The array signature can be color-coded as in, for example, FIG. 1, for easy visual or computer-aided identification. The signature can also be described as a number or series of numbers that correspond to values attributed to the biomarkers identified by the array. The color key shown in FIG. 1 (right side) provides one example of how values can be attributed to biomarker concentrations identified by an array. "Array analysis," as used herein, is the process of extrapolating information from an array using statistical calculations such as factor analysis or principle component analysis (PCA).

In addition to being expressed as a signature, a reference profile can be in the form of a threshold value or series of threshold values. For example, a single threshold value can be determined by averaging the values of a series of cytokine levels from pregnant women having normal pregnancies. Similarly, a single or two or more threshold values can be determined by averaging the values of a series of cytokine levels from pregnant women having a gestational disorder. Thus, a threshold value can have a single value or a plurality of values, each value representing a level of a specific cytokine or growth factor, or antagonist thereof, detected in a urine or blood sample, e.g., of a pregnant individual, or multiple individuals, having a gestational disorder.

For example, FIG. 1 shows that a threshold value for MCP-1 levels derived from samples obtained from pregnant women having normal pregnancies can be calculated based on the average of all 5 urine samples (see "control" horizontal columns for patients designated 262, 104, 102, 35 and 20 and corresponding vertical MCP-1 column). The average level of MCP-1 (assuming 90+230+210+300+210 pg/mL) is approximately 200 pg/mL. A comparison of these data to the MCP-1 levels in urine samples from patients designated 381, 305, 289, 94, and 64 indicates that an MCP-1 level below about 200 pg/mL is indicative of a normal pregnancy. In contrast, a pregnant female having a level of MCP-1 in her urine that exceeds about 200 pg/mL at 16-18 weeks of gestation is predicted to be at risk for developing a gestational disorder. Similarly, urine samples taken from the same patients indicate that an IL-6 level above about 20 pg/mL is indicative of a gestational disorder. Further, urine samples taken from the same patients indicate that an IL-8 level below about 200 pg/mL is indicative of a gestational disorder.

A threshold value can also be a value corresponding to a growth factor, or antagonist thereof, obtained from a urine or non-urine sample, such as serum, plasma, placental tissue, or amniotic fluid. A threshold value can have a single value or plurality of values, each value representing a level of a specific cytokine or growth factor, or antagonist thereof, detected in urine of a pregnant individual, or multiple individuals, that experience a normal pregnancy (i.e., not associated with a gestational disorder as defined herein) or a gestational disorder during pregnancy.

The samples used to generate a profile of the invention can be obtained at between about 6 and 24 weeks, between about 12 and 24 weeks, or between about 18 and 24 weeks after conception. Typically, the sample is taken prior to the third trimester, e.g., at any time between 5 to 24 weeks after conception (e.g., 8, 10, 12, 14, 16, 18, or 20 weeks). For example, urine samples can be obtained from pregnant females at between about 6 and 24 weeks, between about 12 and 24 weeks, or between about 18 and 24 weeks after conception. The sample can be used to generate a subject profile or a reference profile.

A subject profile or reference profile is generated from a sample taken at a given time point in the pregnancy. The sample is typically a urine sample. The subject and reference profiles are generated from samples taken from similar time periods within the subject and reference pregnancies. In general, if a subject profile is generated from a sample taken at week "x" within the subject pregnancy, then the appropriate reference profile for comparison purposes will have been generated from a sample taken at week "x" plus or minus 2 weeks (or 1 week) of the reference pregnancy. For example, a subject profile derived from a sample obtained from a pregnant female estimated to be in her 16th week of pregnancy can be compared with a reference profile, or a plurality of reference profiles, derived from samples obtained from pregnant females in their 14th to 18th or (15th to 17th) week of pregnancy.

As described above, a subject profile can be used to identify a subject at risk for developing a gestational disorder based upon a comparison with the appropriate reference profile or profiles. Women having, or predisposed to having, a gestational disorder can be identified prior to the third trimester of pregnancy by, for example, non-invasive urinalysis. Most previous studies examining informative biomarkers, such as cytokines and growth factors, have not been prospective, nor have the biomarkers been identified in urine. A biomarker can be a cytokine, a growth factor, or a growth factor inhibitor. For example, a subject profile that includes the level of at least two cytokines detected in a urine sample from a subject and comparing the subject profile to a "reference" profile that includes the level of at least two cytokines detected in a urine sample obtained from a normal pregnant subject. Alternatively, the cytokine, growth factor, or growth factor inhibitor levels of the subject profile may correspond to a reference profile, i.e., the subject profile comprises levels of biomarkers that are similar to a reference profile. If the reference profile is derived from a sample obtained from a reference subject having a normal pregnancy, then the similarity of the subject profile to the reference profile is indicative of a normal (non-gestational disorder-associated) pregnancy for the tested subject. Alternatively, if the reference profile is derived from a sample obtained from a reference subject having a gestational disorder, then the similarity of the subject profile to the reference profile is indicative of a gestational disorder-associated pregnancy for the tested subject.

Cytokines

The cytokines can be one or more immune/hematopoietins, interferons, tumor necrosis factors (TNF)-related molecules, or chemokines. Examples include interleukin (IL)-1α, IL-1β, IL-2, IL-4, TNF-α, TNF-R, IL-6, monocyte chemoattractant protein (MCP-1), IL-8, IL-11, IL-12, and VCAM, or any combination thereof. Cytokines comprise a vast array of relatively low molecular weight, pharmacologically active proteins that are secreted by cells for the purpose of altering either their own functions (autocrine effect) or those of adjacent cells (paracrine effect). In many instances, individual cytokines have multiple biological activities. Different cytokines can also have the same activity, which provides for functional redundancy within the inflammatory and immune systems. As a result, it is infrequent that loss or neutralization of one cytokine will markedly interfere with either of these systems. This fact has great significance in the development of therapeutic strategies.

Cytokines can be subdivided into several groups, including the immune/hematopoietins, interferons, tumor necrosis factor (TNF)-related molecules, and the chemokines. Representative immune/hematopoietins include erythropoietin (EPO), granulocyte/macrophage colony-stimulating factor (GM-CSF), granulocyte colony-stimulating factor (G-CSF), leukemia inhibition factor (LIF), oncostatin-M (OSM), ciliary neurotrophic factor (CNTF), growth hormone (GH), prolactin (PRL), interleukin (IL)-1, IL-2, IL-3, IL-4, IL-5, IL-6, IL-7, IL-9, IL-10, and IL-12. Representative interferons (IFN) include IFNα IFNβ, and IFN-gamma.

Representative TNF family members include TNFα, TNF receptors, interferon (IFN)β, $gp^{39}$ (CD40-L), CD27-L, CD30-L, and nerve growth factor (NGF).

Representative chemokines include platelet factor (PF4), platelet basic protein (PBP), groα, MIG, ENA-78, macrophage inflammatory protein (MIP)1α, MIP1β, monocyte chemoattractant protein (MCP)-1,1-309, HC14, C10, Regulated on Activation, Normal T-cell Expressed, and Secreted (RANTES), and IL-8.

Chemokines are a family of structurally related glycoproteins with potent leukocyte activation and/or chemotactic activity. They are 70 to 90 amino acids in length and approximately 8 to 10 kDa in molecular weight. Most of them fit into two subfamilies with four cysteine residues. These subfamilies are distinguished by whether the two amino terminal cysteine residues are immediately adjacent to each other or separated by one amino acid. The α chemokines, also known as CXC chemokines, contain a single amino acid between the first and second cysteine residues; β, or CC, chemokines have adjacent cysteine residues. Most CXC chemokines are chemoattractants for neutrophils whereas CC chemokines generally attract monocytes, lymphocytes, basophils, and eosinophils. There are also 2 other small sub-groups. The C group has one member (lymphotactin). It lacks one of the cysteines in the four-cysteine motif, but shares homology at its carboxyl terminus with the C-C chemokines. The C chemokine seems to be lymphocyte specific. The fourth subgroup is the C-X3-C subgroup. The C-X3-C chemokine (fractalkine/neurotactin) have three amino acid residues between the first two cysteines. They are tethered directly to the cell membrane via a long mucin stalk and induce both adhesion and migration of leukocytes.

A heat map of the cytokine array in urine, serum, and plasma shown in FIG. 1 demonstrates that among women who developed preeclampsia ("cases"), IL-6 is elevated and IL-8 is reduced (see white circle) in the urine at 16-18 weeks of gestation compared to women who had a normotensive pregnancy and with urine samples collected at the same time. This is the first time an array of cytokines was measured in urine by this sensitive technique and the first time differences were seen in urine at this early stage of pregnancy. FIG. 1 also demonstrates that at 16 weeks of gestation the levels of another chemokine, MCP-1, were elevated in the urine of cases as compared to controls. All protein measurements were normalized for urine creatinine concentrations.

Growth Factors

The new methods further include measuring the level of at least one growth factor derived from blood, serum, or placental tissue. Growth factors include placental soluble fms-like tyrosine kinase 1 (sFlt1), VEGF, and placental growth factor (PlGF). SFlt1, a splice variant of the VEGF receptor lacking the transmembrane and cytoplasmic domains, acts as a potent VEGF and PlGF antagonist. Sflt1 is known to be upregulated in preeclampsia, leading to increased systemic levels of sFlt1 that fall after delivery (Maynard et al., J. Clinical Invest., 111: 5, 2003, incorporated herein by reference). Increased circulating sFlt1 in patients with preeclampsia is associated with decreased circulating levels of free VEGF and PlGF.

Placental growth factor (PlGF), a member of the vascular endothelial growth factor (VEGF) family of angiogenic factors (58% sequence identity to VEGF), and other placental VEGF's can contribute to the pathogenesis of GDM and PIH. Furthermore, cytokines and growth factors appear to cooperate in the progression of certain pathological disorders. For example, IL-6 is known to promote cervical and pancreatic cancer and multiple myeloma activity. These processes are also mediated by VEGF (Wei et al., Oncogene, 22: 1517, 2003.). In addition, TNF-α is involved in VEGF secretion by myeloma cells (Alexandrakis et al., Ann Hematol, 82: 19, 2003). Growth factors and cytokines can act on the same target cells, as VEGF and IL-8 both activate monocytes and endothelial cell proliferation, and IL-8 itself can be involved in angiogenesis. Growth factors and cytokines may regulate each other, as PlGF not only activates monocytes, it also increases transcription of inflammatory cytokines (TNF-α, IL-1β) and chemokines (MCP-1, IL-8) (Selvaraj et al., Blood, 2003.). Finally, growth factors may counterbalance cytokine-mediated injury, as TNF-α induces apoptosis of trophoblast cells, and placental growth factors, such as fibroblast growth factor-2 (FGF-2), mitigate this process (Garcia-Lloret et al., J Cell Physiol, 167: 324, 1996). The function of cytokines and growth factors are likely intertwined, in that normal function of both are necessary for normal placental development, and hence alterations in both may lead to a gestational disorder. Simultaneous examination of both can provide a more accurate method for identifying whether a subject has, or is predisposed to having, a gestational disorder.

The new methods can also use alterations in the levels of a combination of cytokines and/or growth factors as indicators of future disease. For example, one case subject had a urinary PlGF level of 91.2 pg/gCr (high, not consistent with PE), but had an IL-6 level of 58 pg/gCr (high, consistent with PE), and an MCP-1 level of 460 pg/gCr (high, consistent with PE). Thus, a urine measurement of a single marker, PlGF, would have incorrectly suggested that this woman was not at risk for PE, but examination of IL-6 and MCP-1 levels would have suggested just the opposite. In another example, in a control subject, the PlGF level was 115.2 pg/gCr (high, consistent with low risk of PE) and IL-6 levels were 20 pg/gCr (low, consistent with low risk for PE), but MCP-1 level was 410 pg/gCr (high, consistent with high risk for PE), therefore, utilizing only MCP-1 levels would have incorrectly predicted her outcome. Therefore, the new methods also encompass the use of patterns of levels of cytokines and growth factors in serum and urine to determine a subject's predisposition to a future disease associated with pregnancy-induced hypertension.

In another embodiment, the invention provides a method of identifying a gestational disorder by comparing the level of IL-1α, IL-1β, IL-2, IL-4, IL-11, IL-12, IFN-γ TNF-α, IL-6, IL-8, or MCP-1, or any combination thereof, in a first biological sample from a pregnant subject the cytokine level in a second biological sample obtained from the same pregnant subject. A difference in the level of a cytokine, or any combination of cytokines, in the first sample as compared to the second sample is indicative of a subject having, or predisposed to having, a gestational disorder. The first and second biological samples can be selected from urine, blood, serum, amniotic fluid or placental tissue.

An exemplary biochemical test for identifying specific proteins, such as cytokines, growth factors, or antagonists thereof, employs a standardized test format, such as the Enzyme Linked Immunosorbent Assay or ELISA test, although the information provided herein may apply to the development of other biochemical or diagnostic tests and is not limited to the development of an ELISA test (see, e.g., Molecular Immunology: A Textbook, edited by Atassi et al. Marcel Dekker Inc., New York and Basel 1984, for a description of ELISA tests).

It is understood that commercial assay enzyme-linked immunosorbant assay (ELISA) kits for various cytokines and growth factors are available. For example, with regard to growth factors such as sFlt-1, PlGF, and FGF-2, ELISA kits are available from R&D systems. These kits can measure free or unbound proteins. The intra-assay precision CV (%) for sFlt-1 and PlGF are about 3.5 and 5.6 respectively. The inter-assay precision CV(%) for sFlt-1 and PlGF are about 8.1 and 10.9 respectively. For serum FGF-2 measurements, the intra-assay and inter-assay CV(%) are about 8 and 12.7 respectively. For urine PlGF and FGF-2, the intra-assay and inter-assay CV(%) are about 11, 9.8, 12.1 and 14.4, respectively.

Proteomics and Microarrays

The new methods can be used to predict adverse outcomes of pregnancy well before the end of the pregnancy through the use of proteomics. Proteomics is an evolving technology capable of testing for the presence of minute amounts of a vast array of proteins using small samples of human tissue. Using proteomic tools, increased or decreased levels of certain proteins in a biological sample such as urine, serum, amniotic fluid or placental tissue can be ascertained. The invention encompasses urine proteomic analysis as a non-invasive approach to diagnosing pregnancy complications remote from term. In addition, using mathematical algorithms a complex proteome or "fingerprint" can be obtained. As previously noted, such algorithms include "factor analyses" and "principle component analysis (PCA)." The proteome can consist of a group of proteins, some increased in concentration from normal and others decreased, that are diagnostic of gestational disorders, such as those associated with PIH and/or GDM.

The invention also provides an array (i.e., "biochip" or "microarray") that includes immobilized biomolecules that facilitate the detection of a particular molecule or molecules in a biological sample. Biomolecules that identify the biomarkers described herein or shown in FIG. 1 can be included in a custom array for detecting subjects predisposed to GDM and/or PIH. For example, a custom array can include biomolecules that identify specific cytokines such as IL-1, IL-2, IL-6, IL-8, VCAM, and MCP-1. The array can also include biomolecules that identify growth factors, such as FGF-2 and PlGF. The array can further include a biomolecule that identifies a growth factor antagonist, such as sFlt-1. Arrays comprising biomolecules that specifically identify selected biomarkers (e.g., a cytokine or a growth factor or antagonist thereof) can be used to develop a database of information using data provided herein. Additional biomolecules that identify cytokines and/or growth factors that lead to improved cross-validated error rates in multivariate prediction models (e.g., logistic regression, discriminant analysis, or regression tree models) can be included in a custom array of the invention.

Customized arrays provide an opportunity to study the biology of GDM and PIH. Standard p values of significance (0.05) can be chosen to exclude or include additional specific biomolecules on the microarray that identify particular biomarkers. In addition, the new arrays can be used to determine whether one cytokine alters the strength of association of another cytokine, even if that protein itself is not significantly associated with the outcome (e.g., is predictive of GDM or PIH).

The term "array," as used herein, generally refers to a predetermined spatial arrangement of binding islands or biomolecules. Arrays according to the present invention that include biomolecules immobilized on a surface can also be referred to as "biomolecule arrays." Arrays that comprise surfaces activated, adapted, prepared, or modified to facilitate the binding of biomolecules to the surface can also be referred to as "binding arrays." Further, the term "array" is used herein to refer to multiple arrays arranged on a surface, such as would be the case where a surface bears multiple copies of an array. Such surfaces bearing multiple arrays may also be referred to as "multiple arrays" or "repeating arrays." The use of the term "array" herein encompasses biomolecule arrays, binding arrays, multiple arrays, and any combination thereof; and the appropriate meaning will be apparent from context. An array can include cytokine-specific biomolecules that detect cytokines and other proteins altered in a gestational disorder.

The biological samples used in the new methods and with the new arrays include fluid or solid samples from any tissue of the body including excretory fluids such as urine. Non-urine samples include, but are not limited to serum, plasma, amniotic fluid, and placental tissue.

An array of the invention comprises a substrate. By "substrate" or "solid support" or other grammatical equivalents, is meant any material appropriate for the attachment of biomolecules and is amenable to at least one detection method. There are many possible substrates including, but not limited to, glass and modified or functionalized glass, plastics (including acrylics, polystyrene and copolymers of styrene and other materials, polypropylene, polyethylene, polybutylene, polyurethanes, and TEFLON®), polysaccharides, nylon or nitrocellulose, resins, silica or silica-based materials including silicon and modified silicon, carbon, metals, inorganic glasses, plastics, ceramics, and a variety of other polymers. In addition, as is known in the art, the substrate may be coated with any number of materials, including polymers, such as dextrans, acrylamides, gelatins or agarose. Such coatings can facilitate the use of the array with a biological sample derived from urine or serum.

A "planar" array will generally contain addressable locations (e.g., "pads", "addresses" or "micro-locations") of biomolecules in an array format. The size of the array will depend on the composition and end use of the array. Arrays containing from about 2 different biomolecules to many thousands can be made. Generally, the array will comprise from two to as many as 100,000 or more, e.g., 5, 10, 25, 50, 100, or more different biomolecules, depending on the end use of the array. A microarray of the invention will generally comprise at least one biomolecule that identifies or "captures" a biomarker, such as a cytokine, growth factor, or antagonist thereof, present in a biological sample. In some embodiments, the compositions described herein may not be in an array format; that is, for some embodiments, compositions comprising a single biomolecule may be made as well. In addition, in some arrays, multiple substrates may be used, either of different or identical compositions. Thus, for example, large planar arrays may comprise a plurality of smaller substrates.

As an alternative to planar arrays, bead-based assays in combination with flow cytometry have been developed to perform multi-parametric immunoassays. In bead-based assay systems the biomolecules can be immobilized on addressable microspheres. Each biomolecule for each individual immunoassay is coupled to a distinct type of microsphere (i.e., "microbead") and the immunoassay reaction takes place on the surface of the microspheres. Dyed microspheres with discrete fluorescence intensities are loaded separately with their appropriate biomolecules. The different bead sets carrying different capture probes can be pooled as necessary to generate custom bead arrays. Bead arrays are then incubated with the sample in a single reaction vessel to perform the immunoassay.

Product formation of the biomarker with their immobilized capture biomolecules can be detected with a fluorescence-based reporter system. Biomarkers, such as cytokines, growth factors or antagonists thereof, can either be labeled directly by a fluorogen or detected by a second fluorescently labeled capture biomolecule. The signal intensities derived from captured biomarkers are measured in a flow cytometer. The flow cytometer first identifies each microsphere by its individual color code. Second, the amount of captured biomarkers on each individual bead is measured by the second color fluorescence specific for the bound target. This allows multiplexed quantitation of multiple targets from a single sample within the same experiment. Sensitivity, reliability and accuracy are compared to standard microtiter ELISA procedures. With bead-based immunoassay systems cytokines can be simultaneously quantified from biological samples. An advantage of bead-based systems is the individual coupling of the capture biomolecule to distinct microspheres.

Thus, microbead array technology can be used to sort cytokines, growth factors, or growth factor antagonists, bound to a specific biomolecule using a plurality of microbeads, each of which can carry about 100,000 identical molecules of a specific anti-tag biomolecule on the surface of a microbead. Once captured, the biomarker, such as a cytokine, can be handled as fluid, referred to herein as a "fluid microarray."

Microarrays as described herein can be biochips that include a high density of immobilized arrays of recognition molecules (e.g., antibodies), where biomarker binding is monitored indirectly (e.g., via fluorescence). In addition, an array can be of a format that involves the capture of proteins by biochemical or intermolecular interaction, coupled with direct detection using a label-free detection method. Such methods include, but are not limited to, surface plasmon resonance, micro-electro-mechanical systems (e.g., cantilevers), semiconductor nanowires, and mass spectrometry (MS).

Arrays and microarrays that can be used with the new methods to detect the biomarkers described herein can be made, for example, according to the methods described in U.S. Pat. Nos. 6,329,209; 6,365,418; 6,406,921; 6,475,808; and 6,475,809, and U.S. patent application Ser. No. 10/884,269, which are incorporated herein in their entirety. For example, the Zyomyx Human Cytokine Biochip® provides a highly sensitive protein profiling system for 30 biologically relevant cytokines. New arrays, to detect specific sets of biomarkers described herein can also be made using the methods described in these patents.

Arrays and microarrays described herein further include arrays that have pathogen-encoded cytokine-binding proteins immobilized on a solid surface. For example, poxvirus genes encoding binding activities for TNF type I and type II interferons, interleukin (IL)-1beta, IL-18, and beta-chemokines have been identified. These high-affinity receptors have the potential to act as surrogate antibodies in a number of applications in cytokine quantification and purification and could be potentially useful reagents to complement the existing panel of anti-cytokine, monoclonal, polyclonal, or engineered antibodies that are currently available.

In many embodiments, immobilized biomolecules, or biomolecules to be immobilized, are proteins. One or more types of proteins may be immobilized on a surface. In certain embodiments, the proteins are immobilized using methods and materials that minimize the denaturing of the proteins, that minimize alterations in the activity of the proteins, or that minimize interactions between the protein and the surface on which they are immobilized.

Surfaces for immobilization of biomolecules may be of any desired shape (form) and size. Non-limiting examples of surfaces include chips, continuous surfaces, curved surfaces, flexible surfaces, films, plates, sheets, tubes, and the like. Surfaces preferably have areas ranging from approximately a square micron to approximately 500 cm$^2$. The area, length, and width of surfaces according to the present invention may be varied according to the requirements of the assay to be performed. Considerations may include, for example, ease of handling, limitations of the material(s) of which the surface is formed, requirements of detection systems, requirements of deposition systems (e.g., arrayers), and the like.

In certain embodiments, it is desirable to employ a physical means for separating groups or arrays of binding islands or immobilized biomolecules: such physical separation facilitates exposure of different groups or arrays to different solutions of interest. Therefore, in certain embodiments, arrays are situated within wells of 96, 384, 1536, or 3456 microwell plates. In such embodiments, the bottoms of the wells may serve as surfaces for the formation of arrays, or arrays may be formed on other surfaces and then placed into wells. In certain embodiments, such as where a surface without wells is used, binding islands may be formed or biomolecules may be immobilized on a surface and a gasket having holes spatially arranged so that they correspond to the islands or biomolecules may be placed on the surface. Such a gasket is preferably liquid tight. A gasket may be placed onto a surface at any time during the process of making the array and may be removed if separation of groups or arrays is no longer necessary.

The immobilized biomolecules can bind to molecules present in a biological sample overlying the immobilized biomolecules. Alternatively, the immobilized biomolecules modify or are modified by molecules present in a biological sample overlying the immobilized biomolecules. For example, a cytokine present in a biological sample can contact an immobilized biomolecule and bind to it, thereby facilitating detection of the cytokine. Alternatively, the cytokine or growth factor or antagonist thereof, can contact a biomolecule immobilized on a solid surface in a transient fashion and initiate a reaction that results in the detection of the cytokine absent the stable binding of the cytokine to the biomolecule.

Modifications or binding of biomolecules in solution or immobilized on an array may be detected using detection techniques known in the art. Examples of such techniques include immunological techniques such as competitive binding assays and sandwich assays; fluorescence detection using instruments such as confocal scanners, confocal microscopes, or CCD-based systems and techniques such as fluorescence, fluorescence polarization (FP), fluorescence resonant energy transfer (FRET), total internal reflection fluorescence (TIRF), fluorescence correlation spectroscopy (FCS); colorimetric/spectrometric techniques; surface plasmon resonance, by which changes in mass of materials adsorbed at surfaces may be measured; techniques using radioisotopes, including conventional radioisotope binding and scintillation proximity assays so (SPA); mass spectroscopy, such as matrix-assisted laser desorption/ionization mass spectroscopy (MALDI) and MALDI—time of flight (TOF) mass spectroscopy; ellipsometry, which is an optical method of measuring thickness of protein films; quartz crystal microbalance (QCM), a very sensitive method for measuring mass of materials adsorbing to surfaces; scanning probe microscopies, such as atomic force microscopy (AFM) and scanning electron microscopy (SEM); and techniques such as electrochemical, impedance, acoustic, microwave, and IR/Raman detection. See, e.g., Mere L, et al., "Miniaturized FRET assays and microfluidics: key components for ultra-high-throughput screening," Drug Discov Today 4(8): 363-369 (1999), and references cited therein; Lakowicz J R, Principles of Fluorescence Spectroscopy, 2nd Edition, Plenum Press (1999).

Arrays suitable for identifying a gestational disorder may be included in kits. Such kits may also include, as non-limiting examples, reagents useful for preparing biomolecules for immobilization onto binding islands or areas of an array, reagents useful for detecting modifications to immobilized biomolecules, reagents useful for detecting binding of biomolecules from solutions of interest to immobilized biomolecules, and/or instructions for use. Likewise, arrays comprising immobilized biomolecules may be included in kits. Such kits may also include, as non-limiting examples, reagents useful for detecting modifications to immobilized biomolecules or for detecting binding of biomolecules from solutions of interest to immobilized biomolecules.

Theranostics

The invention provides compositions and methods for the identification of women at high risk for adverse outcomes of pregnancy such that a theranostic approach can be taken to test such individuals to determine the effectiveness of a particular therapeutic intervention (pharmaceutical or non-pharmaceutical) and to alter the intervention to 1) reduce the risk of developing adverse outcomes and 2) enhance the effectiveness of the intervention. Thus, in addition to diagnosing or confirming the presence of or risk for a gestational disorder, the methods and compositions described herein also provide a means of optimizing the treatment of a subject having such a disorder. The invention provides a theranostic approach to treating a gestational disorder by integrating diagnostics and therapeutics to improve the real-time treatment of a subject having, for example, GDH and/or PIH. Practically, this means creating tests that can identify which patients are most suited to a particular therapy, and providing feedback on how well a drug is working to optimize treatment regimens. In the area of diseases associated with pregnancy-induced hypertension, theranostics can flexibly monitor changes in important parameters (e.g., cytokine and/or growth factor levels) over time. For example, theranostic multi-parameter immunoassays specific for a series of diagnostically relevant cytokines can be used to follow the progress of a subject undergoing treatment for PIH. The markers provided herein are particularly adaptable for use in diagnosis and treatment because they are available in easily obtained body fluids such as urine, blood, or serum.

Within the clinical trial setting, a theranostic method or composition of the invention can provide key information to optimize trial design, monitor efficacy, and enhance drug safety. For instance, "trial design" theranostics can be used for patient stratification, determination of patient eligibility (inclusion/exclusion), creation of homogeneous treatment groups, and selection of patient samples that are representative of the general population. Such theranostic tests can therefore provide the means for patient efficacy enrichment, thereby minimizing the number of individuals needed for trial recruitment. "Efficacy" theranostics are useful for monitoring therapy and assessing efficacy criteria. Finally, "safety" theranostics can be used to prevent adverse drug reactions or avoid medication error.

Statistical Analyses

Figure 8:
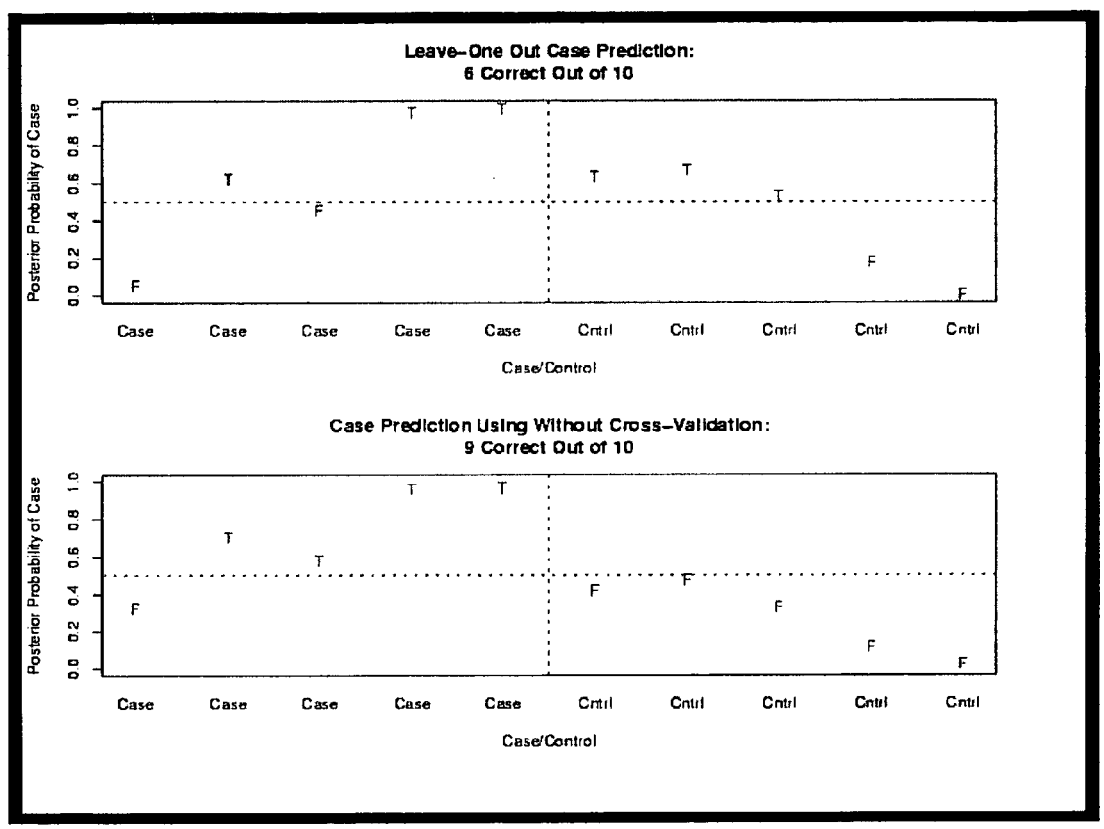
FIG. 8 is a graph that depicts the results of a Bayesian discriminant analysis as applied to the data set of 5 proteins (cytokines) measured on each of 5 cases and 5 controls.

The data presented herein can be used to create a database of information related to diagnosing gestational disorders. Classification and prediction provide a statistical approach to interpreting and utilizing the data generated by an array as shown in FIG. 1. Prediction rules can be selected based on cross-validation, and further validating the chosen rule on a separate cohort. A variety of approaches can be used to generate data predictive of a gestational disorder based on cytokine and/or growth factor levels provided herein, including discriminant analysis, logistic regression, and regression trees. For example, FIG. 8 illustrates a Bayesian discriminant analysis as applied to the data set of 5 proteins (cytokines) measured on each of 5 cases (subjects) and 5 controls (references) shown in FIG. 1.

Discriminant analysis attempts to find a plane in the multivariate space of the marker data such that, to the extent possible, cases appear on one side of this plane, and controls on the other. The coefficients that determine this plane constitute a classification rule: a linear function of the marker values, which is compared with a threshold. In Bayesian classification, information on the probability of a subject being a case (i.e., a subject having, or predisposed to having, a gestational disorder) that is known before the data are obtained can be employed. For example the prior probability of being a case can be set to about 0.5; for a screening test applied to a general population the corresponding probability will be approximately 0.05. A subject is classified as having a complication (i.e., a gestational disorder) if the corresponding posterior probability (i.e., the prior probability updated using the data) exceeds 0.5. Note that 9 of 10 cases and controls are classified correctly (see FIG. 8) when using case prediction without cross-validation, as opposed to leave-one-out case prediction (which shows 6 of 10 correct).

Additional patient information can be combined with the cytokine, growth factor, and growth factor antagonist data provided herein. These data can be combined in a database that analyzes the information to identify trends that complement the present biomarker data. Results can be stored in an electronic format.

The present methods use cytokine and/or growth factor levels as biomarkers for determining the risk for developing various pregnancy complications related to gestational diabetes mellitus or PIH-related disorders, such as preeclampsia and gestational hypertension. Preeclampsia and gestational hypertension develop most commonly in nulliparous (first pregnancy) women who are obese and have high-normal blood pressure at baseline. These disorders also develop in women with a history of preexisting diabetes or gestational diabetes, and in women with polycystic ovary syndrome. In most cases, preeclampsia or gestational hypertension develops without warning, often in women without any of these established risk factors. Accordingly, the methods and compositions for identifying gestational disorder provided herein can be combined with the patient history to enhance the reliability of a medical diagnosis. The analysis can assess, for example, urine or serum biomarkers obtained from the patient through a sample. Further, information concerning the patient can be supplied in conjunction with the test. Such information includes, but is not limited to, age, weight or body mass index, blood pressure, genetic history, and other such parameters or variables as described in the Examples below.

Confounders and covariates in the analysis of data generated to establish guidelines for GDM and PIH can be included in the database of information. These data can include, for example, age, because aging is associated with an increase in circulating inflammatory cytokines. In addition, a correlation between ethnicity and cytokine genetic polymorphisms (IL-6, TNF-α, IL-10) can provide baseline levels of cytokines according to race. Smoking is an example of a confounder, because it can lower sFlt-1 levels, increase VEGF levels, lower cytokine levels, increase risk for GDM, and reduce risk of developing PE. Cytokine and growth factor alteration in women with a history of past and current smoking can be assessed and added to the database of information related to predicting GDM or PIH.

Obesity is a known risk factor for development of GDM and PE, and serum levels of specific cytokines, including TNF-α and IL-6, are both positively correlated with body mass index (BMI). BMI is calculated as the weight in kilograms divided by the square of the height in meters. In addition, growth factors including VEGF are secreted from adipocytes. Elevated BMI may be in the causal pathway, in that obesity leads to elevated cytokines, which leads to insulin resistance and inflammation, which then predisposes to GDM and PIH.

Fetal birth weight can be considered a secondary outcome as GDM and PE lead to increased and decreased fetal birth weights, respectively. This information can be included in a database to determine the association between primary exposures and fetal birth weight in cases (i.e., those subjects exhibiting GDM and/or PIH) and controls. Preeclampsia is one cause of the heterogeneous disorders identified as fetal growth restriction (FGR). Growth factors from the placenta may be involved in the underlying pathophysiology of FGR, and, maternal serum and urine levels of specific growth factors may be altered in women with newborns who have FGR. For example, among women with PE, free PlGF levels at 15-19 weeks of gestation can be lower among women (n=18) who develop PE with small for gestational age newborns (birth weight <10th percentile), compared with women (n=25) who just developed PE. A random selection of nulliparous women can provide uncomplicated pregnancy-controls for comparison purposes. Such women can be, for example, normotensive throughout gestation; normoglycemic, full term (>37 weeks); no evidence of FGR; live birth; no elevated blood pressure or hyperglycemia at the 6 week postpartum visit.

The statistical analyses described above can be correlated with cytokine levels and growth factor levels described in the present specification, such as, TNF-α, IL-1β, IL-6, MCP-1, IL-8, PlGF, FGF-2, and sFlt-1. The primary outcomes will be GDM, PIH, and history of GDM, and PE. Descriptive statistics can be used to spot errors in coding (e.g., outliers), to determine if normality assumptions are met, if transformation is necessary (e.g., log cytokine levels) to improve normality, or if non-parametric approaches are needed. Covariates and confounders distributions can be examined (e.g., contingency tables).

In addition, the statistical analyses generated from the above information can be combined with information regarding growth factor levels and growth factor antagonist levels described herein. Thus, the invention encompasses examining cytokine levels and growth factor levels (and their antagonists) in the same women and correlating this information to identify those individuals predisposed to GDM and/or PIH using additional statistical information such as BMI, blood pressure, fetal birth weight, etc.

Additional analyses can be performed to identify subjects at risk for GDM or PIH. Such analyses include bivariate analysis of each of the primary exposures, multivariate models including variables with a strong relationship (biologic and statistical) with outcomes, methods to account for multiple critical exposures including variable reduction using factor analysis, and prediction models.

For bivariate analysis, the mean level of each primary exposure between cases and controls using a 2-sample t-test or Wilcoxon Rank Sum test, as appropriate, can be conducted. If the association appears linear, trend can be analyzed using the Mantel Haenszel test. Data can be assembled into less fine categories (e.g., tertiles) using the distribution of the controls, and examine these as indicator variables in multivariable analysis.

For multivariate analyses, data can be correlated between two control groups, one matched and another not matched. In both matched and unmatched analyses, the independent effects of all primary exposures of interest can be examined using logistic regression (with conditional models in matched analyses) models. The models can include a minimum number of covariates to test the main effect of specific predictors. The effect of specific proteins can be determined in addition to pregnancy outcomes after accounting for confounders or potentially mediating variables.

Logistic regression models take the general form $[\ln(p_i/1-p_i)=b_0+b_1X1_i+b_2X2_i+\ldots+b_nX_{ni}+e]$, where $p_i$ is the probability of GDM, $b_0$ represents the intercept of the fitted line, $b_1$ is the coefficient associated with a unit increase in the level of a specific cytokine, $b_2 \ldots b_n$ are the coefficients associated with confounding covariates $X2 \ldots Xn$, and e is an error term. The odds ratio associated with a unit increase in the level of a specific cytokine is estimated by exponentiating the coefficient $b_1$, and the 95% confidence interval surrounding this point estimate is estimated by exponentiating the term ($b_1 \pm 1.96$ (standard error of $b_1$)). In models with more than one $b_n$ covariate, the effect of $b_1$ can be interpreted as the effect of the specific cytokine level on risk of GDM and/or PIH after adjustment for levels of confounding covariates included in the model.

In factor analysis, specific cytokines can be reduced to a smaller number of inter-correlated cytokines. Factor scores derived from rotated principal components (which are normally distributed continuous variables) can be modeled instead of original cytokine levels in regression analyses predicting outcomes of pregnancy. This model-building strategy is similar to that described above, but modeling factor scores allowing the identification of specific cytokine signatures as predictive of outcomes independently of other cytokine signatures, or independently of BMI or other important pre-specified confounding or mediating variables.

The diverse array of potentially inter-correlated cytokines and/or growth factors or other biomolecules derived from array experiments can be reduced with factor analysis using principal component analysis. Principal component analysis identifies subsets of correlated variables that group together. These subsets define components: mathematically derived variables that are uncorrelated with each other and that explain the majority of the variance in the original data. Principal components analysis (PCA) attempts to identify a minimum number of components needed to effect a diagnosis. After identification, components are transformed, or rotated, into interpretable factors. Interpretation is based on the pattern of correlations between the factors and the original independent variables; these correlations are called loadings. In array experiments, factor patterns represent domains or distinct groupings of cytokines or other biomolecules underlying the overall relationships among the original array of putatively independent cytokine levels. These groupings may be considered as biomolecule, e.g., cytokine signature patterns.

Figures 6, 7:
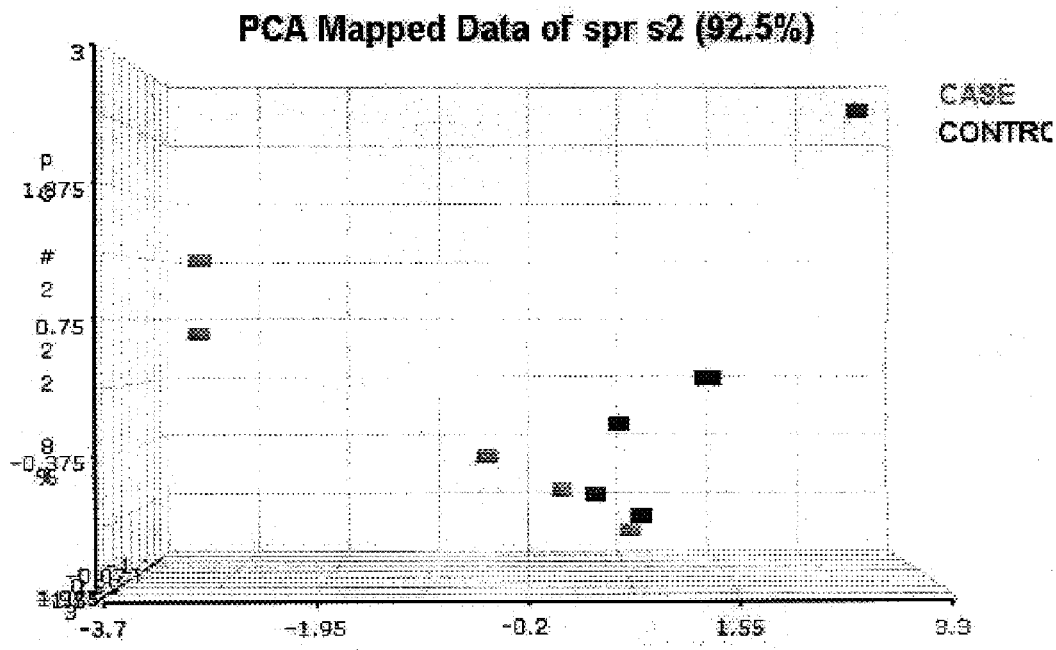
FIG. 6 is a table providing data on serum samples from women with a history of GDM, PE, and normoglycemic/normotensive uncomplicated pregnancy (UP).
FIG. 7 is a three-dimensional graph of the results of a principal components analysis (PCA) of "case" (i.e., "subject") versus "control" (i.e., reference") growth factor data.

Using the patient data described in FIGS. 2 and 3, PCA analysis as shown in FIG. 7 was used to reduce the 5 explanatory cytokines (TNF-α, IL-1β, IL-6, MCP-1, and IL-8) to 3 components, and showing that a separation is beginning to appear between cases (5 most left boxes—lighter gray rectangles) and controls (5 most right boxes—black rectangles). Factor analysis was performed using continuously distributed variables with the principal component option of the SAS FACTOR procedure. Variables may be transformed to improve normality, although principal components are fairly robust to normality deviations. Variables included in the factor analysis include all cytokine levels included in an array experiment, for example. In most cases the minimum number of components are selected based on components whose eigenvalues exceed unity. Eigenvalues are the sum of the squared correlations between the original independent variables and the principal components and represent the amounts of variance attributable to the components.

To avoid over-factored models one generally excludes components with eigenvalues equal to or barely exceeding unity that lie below the inflection point on a screen plot and that do not contribute additional clarity to the resultant factor pattern. To produce interpretable factors, the minimum number of principal components can be rotated using the orthogonal varimax method. This orthogonal rotation is a transformation of the original components that produces factors uncorrelated with each other (representing unique independent domains), but highly correlated with unique subsets of the original cytokines. In general, loadings (correlations between the factors and the original independent variables; range −1.0 to 1.0) greater than ±0.30 are used to interpret the resulting factor pattern. Similarities between loadings on the same factor within selected subgroups (for example, Asian versus White women) can be evaluated using coefficients of congruence. The coefficient of congruence approaches unity when factor loadings are identical between subgroups.

Although factor analysis is not a strict hypothesis testing methodology, one can use Bartlett's method, which gives a value distributed approximately as chi-square, to test the null hypothesis that the first dominant factor may be significant, but remaining factors explain only error variance and are not significant. Confirmatory factor analyses can be conducted to assess whether an empirically determined model (e.g., a three factor solution with two independent variables loading on two factors) provides a better fit to the data than a model with all independent variables loading on a single factor (the null hypothesis model). Three goodness-of fit indices are generally employed: (i) the maximum likelihood goodness-of-fit index, which gives a value distributed as chi-square and where a smaller value indicates a better fit to the data, (ii) Bentler's non-normed fit, and (iii) Bentler and Bonett's comparative fit indices, where higher values (range, 0 to 1.0) indicate a better fit.

Databases and Computerized Methods of Analyzing Data

A database generated from the methods provided herein and the analyses described above can be included in, or associated with, a computer system for determining whether a pregnant subject has, or is predisposed to having, a gestational disorder. The database can include a plurality of digitally encoded "reference" (or "control") profiles. Each reference profile of the plurality can have a plurality of values, each value representing a level of a specific cytokine detected in urine of a pregnant individual having, or predisposed to having, a gestational disorder. Alternatively, a reference profile can be derived from a pregnant individual that is normal. Both types of profiles can be included in the database for consecutive or simultaneous comparison to a subject profile. The computer system can include a server containing a computer-executable code for receiving a profile of a pregnant subject and identifying from the database a matching reference profile that is diagnostically relevant to the pregnant subject profile. The identified profile can be supplied to a caregiver for diagnosis or further analysis.

Using standard programs, electronic medical records (EMR) can be accumulated to provide database that combines cytokine, growth factor and growth factor antagonist data with additional information such as the BMI of a patient or any other parameter useful for predicting the risk of developing GDM or PIH. Patient information can be randomly assigned a numerical identifier to maintain anonymity with testing laboratories and for security purposes. All data are can be stored on a network that provides access to multiple users from various geographic locations.

Thus, the various techniques, methods, and aspects of the invention described above can be implemented in part or in whole using computer-based systems and methods. Additionally, computer-based systems and methods can be used to augment or enhance the functionality described above, increase the speed at which the functions can be performed, and provide additional features and aspects as a part of or in addition to those of the invention described elsewhere in this document. Various computer-based systems, methods, and implementations in accordance with the above-described technology are presented below.

A processor-based system can include a main memory, preferably random access memory (RAM), and can also include a secondary memory. The secondary memory can include, for example, a hard disk drive and/or a storage drive (e.g., a removable storage drive), representing a floppy disk drive, a magnetic tape drive, an optical disk drive, etc. The storage drive reads from and/or writes to a machine-readable (computer-readable) storage medium, which refers to a floppy disk, magnetic tape, optical disk, and the like, which is read by and written to by a storage drive. As will be appreciated, the machine-readable storage medium can comprise computer software and/or data, e.g., in the form of tables, databases, or spreadsheets.

In alternative embodiments, the secondary memory may include other similar means for allowing computer programs or other instructions to be loaded into a computer system. Such means can include, for example, a storage unit and an interface. Examples of such can include a program cartridge and cartridge interface (such as the found in video game devices), a movable memory chip (such as an EPROM or PROM) and associated socket, and other storage units (e.g., removable storage units) and interfaces, which allow software and data to be transferred from the storage unit to the computer system.

The computer system can also include a communications interface. Communications interfaces allow software and data to be transferred between computer system and external devices. Examples of communications interfaces can include a modem, a network interface (such as, for example, an Ethernet card), a communications port, a PCMCIA slot and card, and the like. Software and data transferred via a communications interface are in the form of signals, which can be electronic, electromagnetic, optical, or other signals capable of being received by a communications interface. These signals are provided to communications interface via a channel capable of carrying signals and can be implemented using a wireless medium, wire or cable, fiber optics, or other communications medium. Some examples of a channel can include a phone line, a cellular phone link, an RF link, a network interface, and other communications channels.

Computer programs (also called computer control logic) are stored in main memory and/or secondary memory. Computer programs can also be received via a communications interface. Such computer programs, when executed, enable the computer system to perform the features of the methods described herein. In particular, the computer programs, when executed, enable the processor to perform the features or steps of the new methods. Accordingly, such computer programs represent controllers of the computer system.

In an embodiment where the elements are implemented using software, the software may be stored in, or transmitted via, a computer-readable medium and loaded into a computer system using a removable storage drive, hard drive or communications interface. The control logic (software), when executed by the processor, causes the processor to perform the functions of the methods described herein.

In another embodiment, the elements are implemented primarily in hardware using, for example, hardware components such as PALs, application specific integrated circuits (ASICs), or other hardware components. Implementation of a hardware state machine so as to perform the functions described herein will be apparent to persons skilled in the relevant art(s). In yet another embodiment, elements are implemented using a combination of both hardware and software.

In another embodiment, the computer-based methods can be accessed or implemented over the World Wide Web by providing access via a Web Page to the systems and databases described herein. The Web Page can be identified by a Universal Resource Locator (URL). The URL denotes both the server machine and the particular file or page on that machine. In this embodiment, it is envisioned that a consumer or client computer system interacts with a browser to select a particular URL, which in turn causes the browser to send a request for that URL or page to the server identified in the URL. Typically the server responds to the request by retrieving the requested page and transmitting the data for that page back to the requesting client computer system (the client/server interaction is typically performed in accordance with the hypertext transport protocol ("HTTP")). The selected page is then displayed to the user on the client's display screen. The client may then cause the server containing a computer program of the invention to launch an application to, for example, perform an analysis according to the invention.

EXAMPLES

The invention is further described in the following examples, which serve to illustrate but not to limit the scope of the invention described in the claims.

Example 1

The present example demonstrates that the alteration of even a single cytokine or growth factor can be used to identify subjects having, or predisposed to having, preeclampsia, GDM or GH. Urine, plasma, and serum samples were tested for cytokine levels using a cytokine array (Zyomyx®). The array permits the quantitative analysis of 30 cytokines and chemokines, including IL-1α, IL-3, IL-6, IL-10, IL-12 (p70), TNF-α, MCP-1, CD95 (sFas), IP-10, GM-GSf, IL-1β, IL-4, IL-7, IL-12 (p40), IL-13, TNF-β, MCP-3, MIG, CD23, GCSF, IL-2, IL-5, IL-8, IL-12 (p40/p70), IL-15, Eotaxin, TRAIL, sICAM-1, TGF-β and IFN-γ, using a sample volume of approximately 40 μl of complex biological fluids, such as serum or urine. The data quality is comparable to standards established by ELISA assays. A spike/recovery analysis in urine was carried out and recovery of cytokines in urine (r=0.92) was determined. All subjects had normal renal function, thus it was unlikely urea interfered with the analysis.

Samples from 5 women who developed preeclampsia and 5 controls with normotensive pregnancies were examined for cytokine levels. In all subjects, urine was collected at 16-18 weeks of pregnancy, almost 20 weeks before the clinical diagnosis of gestational disorders. These samples were collected, sorted, and stored at −80° C. until the analyses was performed. The data presented in FIG. 1 show the cytokine array pattern in serum, plasma, and urine from 5 women who subsequently developed PE and 5 women with normotensive pregnancies. All women were nulliparous. Cytokine quantification was carried out with standard calibration techniques using fluorescence intensity.

The heat map of the cytokine array in urine, serum, and plasma shown in FIG. 1 demonstrates that among women who developed preeclampsia ("subject" or "cases"), IL-6 is elevated and IL-8 is reduced (see white circle) in the urine at 16-18 weeks of gestation compared to women who had a normotensive pregnancy ("reference" or "control") and with urine samples collected at the same time. This is the first time an array of cytokines was measured in urine by this sensitive technique and the first time differences were seen in urine for individual cytokines at this early stage of pregnancy.

FIG. 1 also demonstrates that at 16 weeks of gestation the levels of another chemokine, MCP-1, were elevated in the urine of cases as compared to controls. All protein measurements were normalized for urine creatinine concentrations.

The urine samples were further tested to determine whether or not the addition of a standard protease inhibitor (Complete MINI™, Roche) would markedly improve cytokine recovery. As shown in FIG. 2, five urine samples were tested with (+I) and without (−I) addition of the inhibitor (I) at the time of collection. Log transformed (pg/ml) protein profiles (all samples done in duplicate) are shown. As indicated, the recovery of cytokines does not consistently increase in the presence of protease inhibitors. Furthermore, even among samples with elevated cytokine concentrations, there does not appear to be a deterioration of recovery. Finally, reproducibility studies using the cytokine chip were also performed (FIG. 3). These results indicate that the reproducibility of urine cytokine assays is excellent using the biochip array.

Example 2

In conjunction with cytokine levels, the present studies provide information regarding the levels of growth factors in urine and blood samples. Serum and urine samples from 16 weeks of gestation in 15 subjects (5 who developed GDM, 5 PE, and 5 controls) were tested with commercially available ELISA kits for exemplary growth factors sFlt-1, free-VEGF, and free-PlGF (R&D Systems). These ELISA kits have inter-assay and intra-assay CV's of <10%. All assays were performed in duplicate, and the averages are reported in FIG. 4 and FIG. 5. Free-VEGF levels were undetectable and consistent with low VEGF levels generally detected at term.

The data derived from serum samples shown in FIG. 4 indicate that, compared to control women, women who develop GDM have low free PlGF and slightly elevated sFlt-1 levels at 16 weeks of gestation. Moreover, women who subsequently develop PE have even lower free PlGF and higher sFlt-1 levels at this same time period. The balance of anti- to pro-angiogenic factors, reflected by the ratio of sFlt-1/PlGF, differs even at 16 weeks of gestation.

The data derived from urine samples is shown in FIG. 5. Since SFlt-1 is not secreted into urine due to its large size, free PlGF was targeted for identification in the urine sample. Urine cytokine levels were compared with urine PlGF levels. The data in FIG. 5 demonstrates that in general, low free-PlGF levels and elevated IL-6 and MCP-1 levels were strongly associated with subsequent PE.

FIG. 6 presents data on serum samples of women with a history of GDM (n=5), PE (n=5), and normoglycemic/normotensive uncomplicated pregnancy (UP) (n=5) 12±3 months after the incident pregnancy. These data indicate atherogenic and metabolic alterations are present among women with a history of GDM and PE, when compared to women with UP. Importantly, the elevation of CRP and IL-6 suggests persistent subclinical inflammation, and measures of increased insulin resistance (elevated HOMA-IR) and poor insulin secretion (low $\Delta I_{30}/\Delta G_{30}$) suggest increased risk for future type 2 diabetes mellitus. Both features are associated with elevated cytokine levels. In addition, we analyzed IL-6 and TNF-α levels of these same women (GDM v. UP) at 16 weeks of gestation (as described for Example 1) and found that serum IL-6 (GDM 1.7 pg/ml vs. 1.1 pg/ml) and TNF-α (4.37 pg/ml vs. 3.07 pg/ml), and urine IL-6 (GDM 4.24 pg/gCr vs. 1.34 pg/gCr) levels differed. These data indicate that cytokine alterations precede GDM and persist postpartum.

Example 3

The present studies show that differences in urine IL-6 (and serum and urine MCP-1 and urine IL-8) levels at 16 weeks of gestation among women who later developed PE (or GDM) are detectable. In contrast, previous studies have failed to detect such differences (see, e.g., Djurovic et al., BJOG, 109: 759, 2002). As described in Example 1 and shown in FIG. 1, samples from 5 women who developed preeclampsia and 5 controls with normotensive pregnancies were examined for cytokine levels in a urine sample. In all subjects urine was collected at 16-18 weeks of pregnancy, almost 20 weeks before the clinical diagnosis. Using this data, the mean levels of specific proteins at 16 weeks of gestation and postpartum were compared. The differences between means (A), fraction of the standard deviation this represented, and p values are listed in Table 1 below.

TABLE 1

| Urine Cytokines Intrapartum (cases vs. controls) | | |
|---|---|---|
| GDM | | |
| IL-6: | 4.2 vs 1.3 pg/gCr | (Δ 1.2 × SD, p = 0.09) |
| IL-1β: | 1.2 vs 0.7 pg/gCr | (Δ 0.87 × SD, p = 0.27) |
| PE | | |
| IL-6: | 3.6 vs 1.3 pg/gCr | (Δ1 × SD, p = 0.13) |
| IL-8: | 106.2 vs 3.9 pg/ml | (Δ 0.94 × SD, p = 0.18) |
| MCP1: | 494 vs 244 pg/gCr | (Δ 1.1 × SD, p = 0.08) |
| PlGF: | 53.7 vs 71.9 pg/gCr | (Δ 0.89 × SD, p = 0.22) |
| Serum Cytokines (cases vs. controls) | | |
| GDM | | |
| IL-6 (postpartum): | 2.1 vs 1.1 pg/ml | (Δ 0.98 × SD, p = 0.15) |
| TNF-α (intrapartum): | 4.37 vs 3.07 pg/ml | (Δ 0.88 × SD, p = 0.21) |
| PE | | |
| sFlt-1 intrapartum: | 1176 vs 478 pg/m | (Δ 0.99 × SD, p = 0.12) |
| PlGF intrapartum: | 26 vs. 163 pg/ml | (Δ 1.14 × SD, p = 0.08) |

Figures 9, 10, 11:
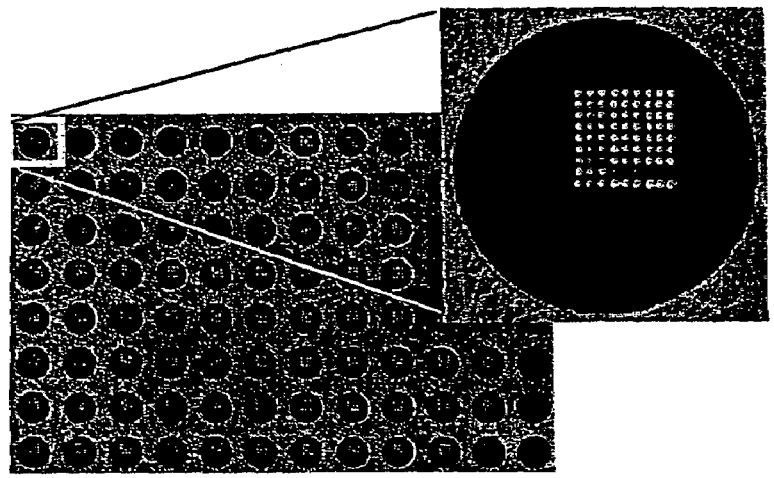
FIG. 9 is a table providing the results for detecting mean differences in cytokine levels in case versus control subjects.
FIG. 10 is a table providing the results of a calculation that detects significant linear trends (chi-square test for trend) across tertiles for identifying the relative risk (RR) of a subject in developing a gestational disorder.
FIG. 11 is a schematic illustration of a 96-well microtiter plate and a close-up of a single well. Each well is imprinted with antibodies to the twenty-five different cytokines (in triplicate) followed by six replicates of directly labeled BSA.

The power (1-3) for detecting mean differences was estimated with standard deviations that differ by 0.75, 1.0, and 1.25 (based on two-sample, two-sided t-tests with a conservative Bonferonni adjusted p of 0.05/8, or 0.006 for 8 pre-specified cytokines) and 1:1 cases:controls. The results are shown in FIG. 9. The data indicate that 60 cases and 60 controls provides at least 90% power to detect a difference in means separated by 0.75 standard deviations or greater. FIG. 10 is a table providing the results of a calculation that detects significant linear trends (chi-square test for trend) across tertiles for identifying the relative risk (RR) of a subject in developing a gestational disorder.

Example 4

In another sample set of cases and controls, urine samples were tested for various cytokines using multiplex techniques on an array similar to the one described in Example 1 above. IL-8 was included because of the positive results from Example 1 described above. As shown in Table 2 below, the results for IL-8 here are similar to those for IL-8 in Example 1, shown in FIG. 1, that is, IL-8 was significantly reduced in the patient urine samples compared to control samples. Other cytokines were also tested for which extensive quality control had been performed. The results in Table 2 below suggest that at least these cytokines (IL-1α, IL-1β, IL-4, IL-8, sTNFRI, and sTNFRII, of the total of 25 tested) are useful to differentiate test cases from controls at an early stage of pregnancy based on urine samples. Others within this group may also be predictive in different settings or in combination with one or more other biomolecules in this group.

In particular, urine samples were tested for cytokine levels using an array of cytokine-specific antibodies, allowing the simultaneous detection of Ang, sICAM-1, IFN-γ, IL-1α, IL-1β, IL-2, IL-4, IL-6, IL-8, IL-11, IL-12(p70), MCP-1, MCSF, MIP-1a, MIP-1β, PlGF, RANTES, TGF-β1, TGF-β3, sTNFRI, sTNFRII, VCAM-1, VEGF, and sFlt-1. The array is shown in FIG. 11, which illustrates a 96-well microtiter plate and a close-up of a single well. Each well was imprinted with antibodies to the twenty-five different cytokines (in triplicate) followed by six replicates of directly labeled BSA. The spots are at a center-to-center distance of 250 mm and each spot has a volume of 350 pL.

All urine samples were diluted: one part urine in three parts HEPES-buffered saline pH 7.4 (HBS) with 15% fetal bovine serum (FBS). For urine with high levels of cytokines, an additional dilution of one part urine in 99 parts HBS with 15% FBS was made. No more than 20 µL of urine was used for any dilution. All subjects had normal renal function, making interference by urea unlikely. The samples were collected, sorted, and stored at −80° C. until thawed on ice and applied to the arrays. The data in Table 2 below shows the concentration of cytokines corrected for creatinine concentration in the urine of pregnant women who subsequently developed preeclampsia (PE) and women with normotensive pregnancies (controls). All women were nulliparous. Cytokine quantification was carried out via a standard curve generated using fluorescence intensity corrected for background and conventional techniques.

TABLE 2

| Cytokine | Preeclampsia (n = 14) | Controls (n = 53) |
| --- | --- | --- |
| IL-8 (pg/ml) | 76.21 | 780.60 |
| IL-1α (pg/ml) | 0.83 | 0.64 |
| IL-1β (pg/ml) | 0.21 | 0.05 |
| IL-4 (pg/ml) | 1.50 | 1.10 |
| sTNF-RI (pg/ml) | 16.83 | 11.29 |
| sTNF-RII (pg/ml) | 39.43 | 34.02 |

These results show that urine levels (creatinine adjusted) of IL-8 were lower in test urine samples than in control urine samples, whereas urine levels of IL-1α, IL-1β, IL-4, sTNF-RI, and sTNF-RII were higher in test cases compared with gestational age matched control women who did not develop preeclampsia. Any two or more of these cytokines (e.g., IL-1α, IL-1β, IL-4, and/or IL-8, or one of the interleukins and one or both of sTNF-RI and sTNF-RII) can be used, e.g., in an array, to detect a gestational disorder, e.g., by using a urine sample.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of determining whether a pregnant human subject has, or is predisposed to having, preeclampsia, the method comprising:
    obtaining a urine sample from the pregnant human subject at between about 16 to 18 or 18 to 24 weeks of gestation;
    measuring levels of at least two specific proteins selected from the group consisting of monocyte chemoattractant protein-1 (MCP-1), soluble TNF receptor I (sTNFR-I), soluble TNF receptor II (sTNFR-II), interleukin (IL)-1α, IL-1β, IL-4, IL-6, and IL-8, in the subject urine sample;
    generating a subject profile comprising at least two values, each value representing a level of one of said specific proteins;
    comparing the subject profile with a reference profile, wherein the reference profile comprises two or more values, each value representing a reference level one of said specific proteins; and
    determining whether the pregnant human subject has, or is predisposed to having, preeclampsia based on the comparison of the subject profile with the reference profile.

2. The method of claim 1, wherein the subject and reference profiles are each generated from urine samples obtained during the same week of pregnancy.

3. The method of claim 2, wherein the subject and reference profiles are each generated from urine samples obtained during the same week of pregnancy at about 16 to 18 weeks after conception.

4. The method of claim 1, wherein measuring the level of at least two specific proteins comprises measuring the level of IL-1β, IL-6, IL-8, or MCP-1, or any combination of three or more thereof.

5. The method of claim 1, wherein measuring the level of at least two proteins comprises measuring the level of IL-6, IL-8, or MCP-1, in any combination of any two thereof, or all three.

6. The method of claim 1, further comprising measuring the level of at least one growth factor in the subject and reference samples.

7. The method of claim 6, wherein the growth factor is selected from the group consisting of fibroblast growth factor-2 (FGF-2), placental growth factor (P1GF), and vascular endothelial growth factor (VEGF).

8. The method of claim 1, further comprising measuring the level of at least one growth factor antagonist in samples comprising blood, serum, or placental tissue from the pregnant subject and reference subject.

9. The method of claim 8, wherein the growth factor antagonist is soluble fms-like tyrosine kinase-1 receptor (sFlt-1).

10. The method of claim 1, wherein the reference profile is obtained from one or more subjects having or predisposed to having preeclampsia.

11. The method of claim 1, wherein the reference profile is obtained from one or more subjects having a normal pregnancy.

12. The method of claim 1, wherein at least one of the two specific proteins is selected from the group consisting of sTNFR-I and sTNFR-II.

13. A method of determining whether a pregnant subject has, or is predisposed to having, preeclampsia, the method comprising:
    obtaining a urine sample from a pregnant subject at between about 16 to 18 or 18 to 24 weeks of gestation;
    measuring levels of two or more specific proteins selected from the group consisting of monocyte chemoattractant protein-1 (MCP-1), soluble TNF receptor I (sTNRF-I), soluble TNF receptor II (sTNFR-II), interleukin (IL)-1α, IL-1β, IL-4, IL-6, and IL-8, in the sample; and
    comparing the levels of said specific proteins in the subject urine sample with the levels of said specific proteins in one or more urine samples obtained from (i) a reference subject having preecalampsia; (ii) a reference subject having a normal pregnancy; or (iii) urine samples from both a reference subject having preeclampsia and a reference subject having a normal pregnancy; and determining whether the pregnant subject has, or is predisposed to having, preeclampsia based on the comparison of the subject levels of said specific proteins with the one or more reference levels of said specific proteins.

14. The method of claim 13, wherein the reference subject has a normal pregnancy, and the pregnant subject is determined to have or to be predisposed to having preeclampsia when the comparison indicates an increase or decrease in the subject levels of said specific proteins compared to the reference levels of said specific proteins.

15. The method of claim 13, wherein measuring the level of one or more cytokines in the sample comprises measuring levels of two or more of IL-1β, IL-6, IL-8, and MCP-1.

16. The method of claim 13, further comprising measuring the level of at least one growth factor in the urine samples obtained from the pregnant subject, a first reference subject having preeclampsia, and a second reference subject having a normal pregnancy.

17. The method of claim 16, wherein the growth factor is selected from the group consisting of fibroblast growth factor (FGF)-2, vascular endothelial growth factor (VEGF) and placental growth factor (P1GF).

18. A method of determining whether a pregnant subject has, or is predisposed to having, preeclampsia, the method comprising:
obtaining a urine sample from a pregnant subject at between about 16 to 18 or 18 to 24 weeks of gestation;
contacting the sample to an array of two or more immobilized antibodies that recognize specific proteins selected from the group consisting of monocyte chemoattractant protein-1 (MCP-1), soluble TNF receptor I (sTNFR-I), soluble TNF receptor II (sTNFR-II), interleukin (IL)-1α, IL-1β, IL-4, IL-6, and IL-8;
obtaining a subject profile corresponding to binding of said antibodies in the array that indicates the levels of said specific proteins in the urine sample from the pregnant subject;
obtaining a reference profile corresponding to binding of said antibodies in the array that indicates the levels of said specific proteins in urine samples from one or more women having a normal pregnancy;
comparing the subject profile with the reference profile, wherein a difference between the subject profile and the reference profile indicates that the subject has, or is predisposed to having, preeclampsia.

19. The method of claim 18, wherein the antibodies are monoclonal antibodies.

20. A method of determining whether a pregnant woman subject has, or is predisposed to having, preeclampsia, the method comprising;
obtaining a urine sample from the pregnant human subject at between about 16 to 18 or 18 to 24 weeks of gestation;
measuring a level of monocyte chemoattractant protein-1 (MCP-1), IL-1β, IL-6, and IL-8,
generating a subject profile comprising values representing the levels of MCP-1, IL-1β, IL-6, IL-8;
comparing the subject profile with a reference profile, wherein the reference profile comprises values representing the levels of MCP-1, IL-1β, IL-6, and IL-8; and
determining whether the pregnant human subject has, or is predisposed to having, preeclampsia based on the comparison of the subject profile with the reference profile.

21. The method of claim 20, wherein the subject and reference urine sample are each obtained during the same week of pregnancy.

22. The method of claim 20, wherein the subject and reference urine samples are each obtained during weeks 16-18 of pregnancy.

23. The method of claim 20, further comprising measuring a level of at least one growth factor in the subject and reference sample.

24. The method of claim 23, wherein the growth factor is selected from the group consisting of fibroblast growth factor-2 (FGF-2), placental growth factor (P1GF), and vascular endothelial growth factor (VEGF).

25. The method of claim 20, further comprising measuring the level of at least one growth factor antagonist derived from blood, serum, or placental tissue in the pregnant subject and reference subject sample.

26. The method of claim 25, wherein the growth factor antagonist is soluble fms-like tyrosine kinase-1 receptor (sFlt-1).

* * * * *